(12) United States Patent
DiFoggio et al.

(10) Patent No.: US 7,523,640 B2
(45) Date of Patent: Apr. 28, 2009

(54) ACOUSTIC FLUID ANALYZER

(75) Inventors: Rocco DiFoggio, Houston, TX (US); Weimin Yao, Kingwood, TX (US)

(73) Assignee: Baker Hughes Incorporated, Houston, TX (US)

( * ) Notice: Subject to any disclaimer, the term of this patent is extended or adjusted under 35 U.S.C. 154(b) by 467 days.

(21) Appl. No.: 11/194,365

(22) Filed: Aug. 1, 2005

(65) Prior Publication Data

US 2007/0022803 A1 Feb. 1, 2007

(51) Int. Cl.
*G01N 29/024* (2006.01)
*G01N 29/44* (2006.01)
*G01N 29/22* (2006.01)

(52) U.S. Cl. .................. 73/19.03; 73/32 A; 73/592; 73/602

(58) Field of Classification Search .............. 73/32 A, 73/629, 64.53, 152.58, 597
See application file for complete search history.

(56) References Cited

U.S. PATENT DOCUMENTS

| | | | | |
|---|---|---|---|---|
| 4,571,693 A | * | 2/1986 | Birchak et al. ............... 702/54 |
| 4,619,267 A | * | 10/1986 | Lannuzel et al. ............ 600/442 |
| 4,769,793 A | * | 9/1988 | Kniest et al. ................. 367/99 |
| 4,938,066 A | * | 7/1990 | Dorr ............................ 73/597 |
| 5,635,626 A | | 6/1997 | Hammond et al. |
| 5,741,962 A | | 4/1998 | Birchak et al. |
| 6,029,507 A | * | 2/2000 | Faber et al. ................. 73/61.75 |
| 6,032,516 A | * | 3/2000 | Takahashi et al. .......... 73/64.53 |
| 6,205,848 B1 | * | 3/2001 | Faber et al. ................. 73/61.75 |
| 6,250,137 B1 | * | 6/2001 | Takahashi et al. .......... 73/64.53 |
| 6,634,214 B1 | | 10/2003 | Thurston et al. |
| 6,672,163 B2 | | 1/2004 | Han et al. |
| 6,817,229 B2 | | 11/2004 | Han et al. |
| 7,024,917 B2 | * | 4/2006 | DiFoggio ..................... 73/30.01 |
| 2002/0100327 A1 | | 8/2002 | Kersey et al. |
| 2002/0117003 A1 | | 8/2002 | Banno et al. |
| 2002/0178787 A1 | | 12/2002 | Matsiev et al. |
| 2002/0178805 A1 | | 12/2002 | DiFoggio et al. |
| 2002/0184940 A1 | | 12/2002 | Storm et al. |
| 2002/0189367 A1 | | 12/2002 | Gomm et al. |
| 2002/0194906 A1 | | 12/2002 | Goodwin et al. |
| 2003/0029241 A1 | | 2/2003 | Mandal |
| 2003/0029242 A1 | | 2/2003 | Varalioglu et al. |
| 2003/0051533 A1 | | 3/2003 | Coupland et al. |
| 2003/0101819 A1 | | 6/2003 | Mutz et al. |
| 2003/0144746 A1 | * | 7/2003 | Hsiung et al. ................. 700/28 |

(Continued)

OTHER PUBLICATIONS

Sitakanta Mohanty, Effect of Multiphase Fluid Saturation on the Thermal Conductivity of Geologic Media, J. Phys. D. Appl. Phys., 30, No. 24 (Dec. 21, 1997), pp. L80-L84.

(Continued)

*Primary Examiner*—Hezron Williams
*Assistant Examiner*—Rose M Miller
(74) *Attorney, Agent, or Firm*—Bracewell & Guiliani LLP

(57) ABSTRACT

A method of determining properties of a formation fluid based on measurements of fluid sound speed, a measurement of fluid density, or both. The properties include compressibility, thermal conductivity, and gas oil ratio. The compressibility of a fluid is equal to the reciprocal of the product of the sound speed squared and fluid density. The density and the sound speed can be measured acoustically. The method further includes a manner of processing data including applying the Savitzky-Golay method and utilizing a variable thresholding technique.

11 Claims, 2 Drawing Sheets

U.S. PATENT DOCUMENTS

| | | |
|---|---|---|
| 2003/0150262 A1 | 8/2003 | Han et al. |
| 2003/0172734 A1 | 9/2003 | Greenwood |
| 2003/0209066 A1 | 11/2003 | Goodwin |
| 2003/0220742 A1* | 11/2003 | Niedermayr et al. ........... 702/9 |
| 2004/0007058 A1 | 1/2004 | Rylander et al. |
| 2004/0020294 A1 | 2/2004 | Buckin |
| 2004/0040746 A1* | 3/2004 | Niedermayr et al. .......... 175/38 |
| 2004/0060345 A1 | 4/2004 | Eggen et al. |
| 2004/0173017 A1 | 9/2004 | O'Brien |
| 2004/0194539 A1 | 10/2004 | Gysling |
| 2004/0216515 A1 | 11/2004 | Yakhno et al. |
| 2004/0236512 A1 | 11/2004 | DiFoggio et al. |
| 2005/0103097 A1 | 5/2005 | Faltum et al. |
| 2005/0149277 A1 | 7/2005 | Bailey et al. |
| 2005/0212869 A1 | 9/2005 | Elison et al. |
| 2005/0223808 A1 | 10/2005 | Myers et al. |
| 2005/0252294 A1 | 11/2005 | Ariav |
| 2005/0268703 A1 | 12/2005 | Funck et al. |

OTHER PUBLICATIONS

Terra E. Bulloch, The Investigation of Fluid Properties and Seismic Attributes for Reservoir Characterization, Thesis for degree of Master of Science in Geological Engineering, Michigan Technological University, 1999, pp. A1-A6.

Abraham Savitzky and Marcel J. E. Golay, Smoothing and Differentiation of Data by Simplified Least Squares Procedures, Analytical Chemistry, International Gas Chromatography Symposium, vol. 36, No. 8, Jul. 1964 —pp. 1627-1639.

Reservoir Characterization Instrument, pamphlet from Baker Hughes, Copyright 2000 Baker Hughes Incorporated.

* cited by examiner

ACOUSTIC FLUID ANALYZER

BACKGROUND OF THE INVENTION

1. Field of the Invention

The invention relates to wellbore evaluation operations. More specifically, the present invention relates to an apparatus and method for ascertaining the compressibility of connate fluid within a wellbore and the presence of a gaseous phase in that fluid.

2. Description of Related Art

The sampling of connate fluid contained in subterranean formations provides a method of testing formation zones of possible interest with regard to hydrocarbon bearing potential. This involves recovering a sample of any formation fluids present for later analysis in a laboratory environment while causing a minimum of damage to the tested formations. The formation sample is essentially a point test of the possible productivity of subsurface earth formations. Additionally, a continuous record of the control and sequence of events during the test is made at the surface. From this record, valuable formation pressure and permeability data as well as data determinative of fluid compressibility, density and viscosity can be obtained for formation reservoir analysis.

Generally connate fluid sampling involves disposing a sonde 10 into a wellbore 5 via a wireline 8. Oppositely located on the outer portion of the sonde 10 usually are a sample port 14 and an urging means 12. When the sample port 14 is proximate to a formation of interest 6, the urging means 12 is extended against the inner surface of the wellbore 5 thereby engaging the sample port 14 into the formation 6. The engagement of the sample port 14 pierces the outer diameter of the wellbore 5 and enables fluid communication between the connate fluid in the formation 6 and the sample port 14. As will be described in more detail below, after urging the sample port 14 into the formation 6, the connate fluid can be siphoned into the sonde 10 with a pumping means disposed therein.

Downhole multi-tester instruments have been developed with extendable sampling probes that engage the borehole wall and withdraw fluid samples from a formation of interest as well as measure pressure of the fluid within the formation. Traditionally these downhole instruments comprise an internal draw-down piston that is reciprocated hydraulically or electrically for drawing connate fluid from the formation to the instrument.

Generally, the downhole multi-test sampling devices incorporate a fluid circuit for the sampling system which requires the connate fluid extracted from the formation, together with any foreign matter such as fine sand, rocks, mud-cake, etc. encountered by the sampling probe, to be drawn into a relatively small volume chamber and which is discharged into the borehole when the tool is closed. An example of such a device can be found in U.S. Pat. No. 4,416,152. Before closing, a sample can be allowed to flow into a sample tank through a separate but parallel circuit. Other methods provide for the sample to be collected through the same fluid circuit.

When exposed to an open hole, the fluid characteristics of formation fluid can change rapidly, thus it is important that the formation fluid be removed as quickly as possible. However, it is important that the formation flow rate be regulated in order to prevent dropping the fluid pressure below its "bubble-point" since measuring separated fluids does not result in a representative sample. After having these components come out of solution, they typically cannot be easily recombined which results in an unrepresentative sample having altered fluid properties.

Recently developed reservoir testing devices illustrate one method of measuring the bubble-point pressures of the connate fluid at the time of sample collection. This can be accomplished using known techniques of light transmissibility to detect bubbles in the liquid. However this method has some drawbacks when particulate matter is present in the fluid thereby resulting in possible erroneous results. Other methods include trapping a known volume of formation fluid and increasing its volume gradually at a constant temperature. The measured changes in volume and pressure provide a plot of pressure versus volume in order to ascertain the value of the bubble-point. This value is estimated within the region of the plot where the pressure change with volume first deviates from the initial straight line.

Unfortunately the pumping devices currently in use with the above described sampling devices have some inherent drawbacks. For example, control of the electrical or hydraulic actuation means of the presently used pumping systems is not accurate that in turn results in an inability to fully control the speed of the pumps. Not being able to fully control pump speed prohibits the capability of ceasing pumping operations should the pressure of the connate fluid fall below its bubble point and also hinders the ability to accurately measure the bubble point. Since sampling connate fluid at pressures below its bubble point negatively affects the accuracy of the sampling data results. Therefore a need exists for a means of accurately analyzing properties of connate fluid without affecting the condition or state of the fluid.

BRIEF SUMMARY OF THE INVENTION

The present invention includes a method of estimating a fluid property comprising, generating an external acoustic signal, measuring the signal travel time through the fluid, determining the fluid density, determining the fluid sound speed based on the measured travel time, and calculating the property of the fluid based on the fluid density and the fluid sound speed. The step of determining fluid density of the present method is based on the measured time travel. The method further includes placing a sample of fluid within the vessel in communication with a signal generator and activating the signal generator to create acoustic signal reverberations within the fluid.

The step of generating a signal external to the vessel can be performed with a device such as a piezoelectric device, an electromagnetic acoustic transmitter, a pulsed laser, or a flexural resonator. The fluid property being determined can include fluid compressibility, fluid thermal conductivity, and fluid gas oil ratio. The value of the fluid compressibility is the reciprocal of the product of the fluid sound speed squared and the fluid density. The method disclosed herein can also include determining the presence of gas within the fluid, where the presence of gas is detected based on a signal strength ranging from no response to a low response.

The method can further comprise processing the measured signal travel time with the Savitzky-Golay method. The method can also further comprise processing the measured signal with a variable threshold method.

Also disclosed herein is a sampling device comprising a container having fluid therein, a signal generator in cooperation with the container, and a receiver in cooperation with the container. The receiver is capable of recording signal travel through the fluid, wherein the fluid sound speed can be determined by analyzing the signal travel time, and wherein a fluid property can be determined based on the fluid density and fluid sound speed. The fluid property being determined includes compressibility, density, gas oil ratio, gas content, bubble point, and thermal conductivity. The sampling device can further include a processor in cooperation with the receiver for calculating the fluid property. The signal generator can also act as a receiver. The fluid being sampled can be downhole connate fluid.

The signal generator of the sampling device can be a piezoelectric device, an EMAT, a pulsed laser, or a flexural resonator.

Further included is a method of determining fluid density comprising, generating a signal, passing the signal through a fluid, measuring the signal travel time through the fluid, and determining the fluid density based on the measured signal travel time. The method of determining fluid density can further comprising determining the fluid compressibility based on the determined fluid density and the measured signal travel time. The step of generating a signal and passing the signal through a fluid, while determining density, is accomplished by placing a sample of fluid within a vessel in communication with a signal generator and activating the signal generator thereby creating an acoustic signal within the fluid. The step of generating a signal is performed with a device such as a piezoelectric device, an EMAT, a pulsed laser, and a flexural resonator. The method of determining fluid density can also include determining the presence of gas within the fluid. The presence of gas is detected based on a signal strength ranging from no response to a low response. The method of determining fluid density can further include measuring the thermal conductivity of the fluid and using the measured thermal conductivity to determine the fluid density.

A method of determining the thermal conductivity of a fluid is included herein. This method comprises, generating a signal, passing the signal through the fluid, measuring the signal travel time through the fluid, determining the fluid density, determining the fluid sound speed based on the measured travel time, and calculating the thermal conductivity of the fluid based on the fluid density and the fluid sound speed. The thermal conductivity of the fluid, with regard to the method of determining thermal conductivity, is equal to the following product; (p)(k)(c)(N), where p=a proportionality constant ranging from 2.8 to 3.0, k=Boltzmann's constant, c=fluid sound speed, and N=molecules per unit volume of the fluid. The fluid being analyzed in determining thermal conductivity can be a connate fluid. The method of determining the thermal conductivity may further comprise disposing the fluid within a vessel. The step of generating a signal for determining thermal conductivity is performed with a device such as a piezoelectric device, an EMAT, a pulsed laser, or a flexural resonator.

Further included with the present methods and apparatus is a method of determining the gas oil ratio of a fluid comprising, generating a signal, passing the signal through the fluid, measuring the signal travel time through the fluid, determining the fluid sound speed based on the measured travel time, and calculating the gas oil ratio of the fluid based on the fluid sound speed. The fluid under consideration in the method of determining the gas oil ratio of a fluid is a downhole connate fluid. The step of generating a signal is performed with a device selected from the list consisting of a piezoelectric device, an EMAT, a pulsed laser, and a flexural resonator.

DETAILED DESCRIPTION OF THE INVENTION

Figure 2:
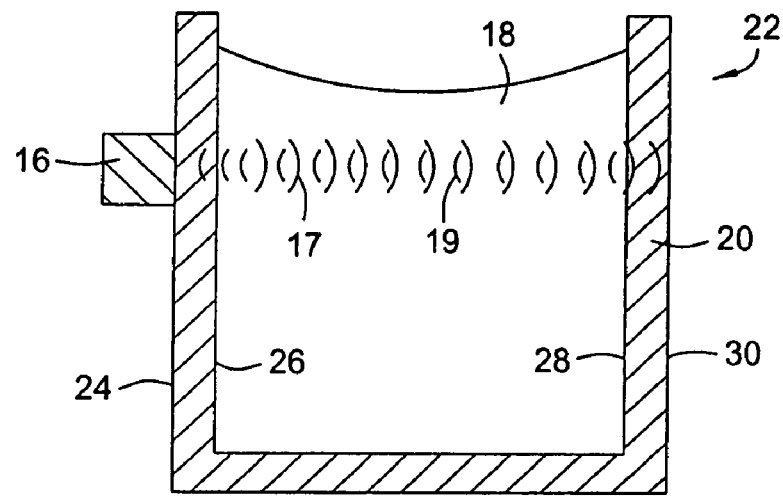
FIG. 2 illustrates a cut-away view of a sampling system.

The method disclosed herein provides a manner of evaluating the compressibility of a fluid based on the measured fluid density and measured sound speed of the fluid. With reference now to FIG. 2, an embodiment of a sampling system 22 of the present device is illustrated in a partial cut-away view. The sampling system 22 of FIG. 2 comprises a vessel or container 20 in cooperation with a signal generator 16. The outer surface of the container 20 can have a radial or rectangular configuration as well as the shape of a tubular. Optionally the vessel or container 20 can be comprised of a conduit or pipe.

As shown, the container 20 should be capable of retaining and storing the fluid 18 within its confines during analysis. Although shown as open at its top, the container 20 can also be sealed thereby fully encapsulating the fluid 18 therein. The signal generator 16 can be attached to the outer or first wall 24 of the container 20 or maintained in place. As will be described herein below, for the purposes of reference, both the first and second walls (24, 26) shown adjacent to the signal generator 16 are shown as well as the third and fourth walls (28, 30) distal from the signal generator 16.

With respect to the signal generator 16, it can be comprised of any device capable of producing a recordable acoustic signal that passes through the fluid. This includes traditional acoustic devices such as piezoelectric devices, however other acoustic transducers can also be used to accomplish this function. For example, an Electro-Magnetic Acoustic Transducer (EMAT) can insert ultrasonic waves into metal by electromagnetic coupling. Alternatively, a pulsed laser that strikes an object can generate acoustic waves at a frequency that depends on the laser pulse frequency. Moreover, the signal generator 16 can also be used as a receiver for receiving and recording reflections of the signals generated by the signal generator 16. One example of a flexural mechanical resonator useful with the device disclosed herein is described in detail in Patent Publication No.: U.S. 2002/017885 having Ser. No. 10/144,965 published Dec. 5, 2002, the disclosure of which is incorporated for reference herein in its entirety.

Figure 1:
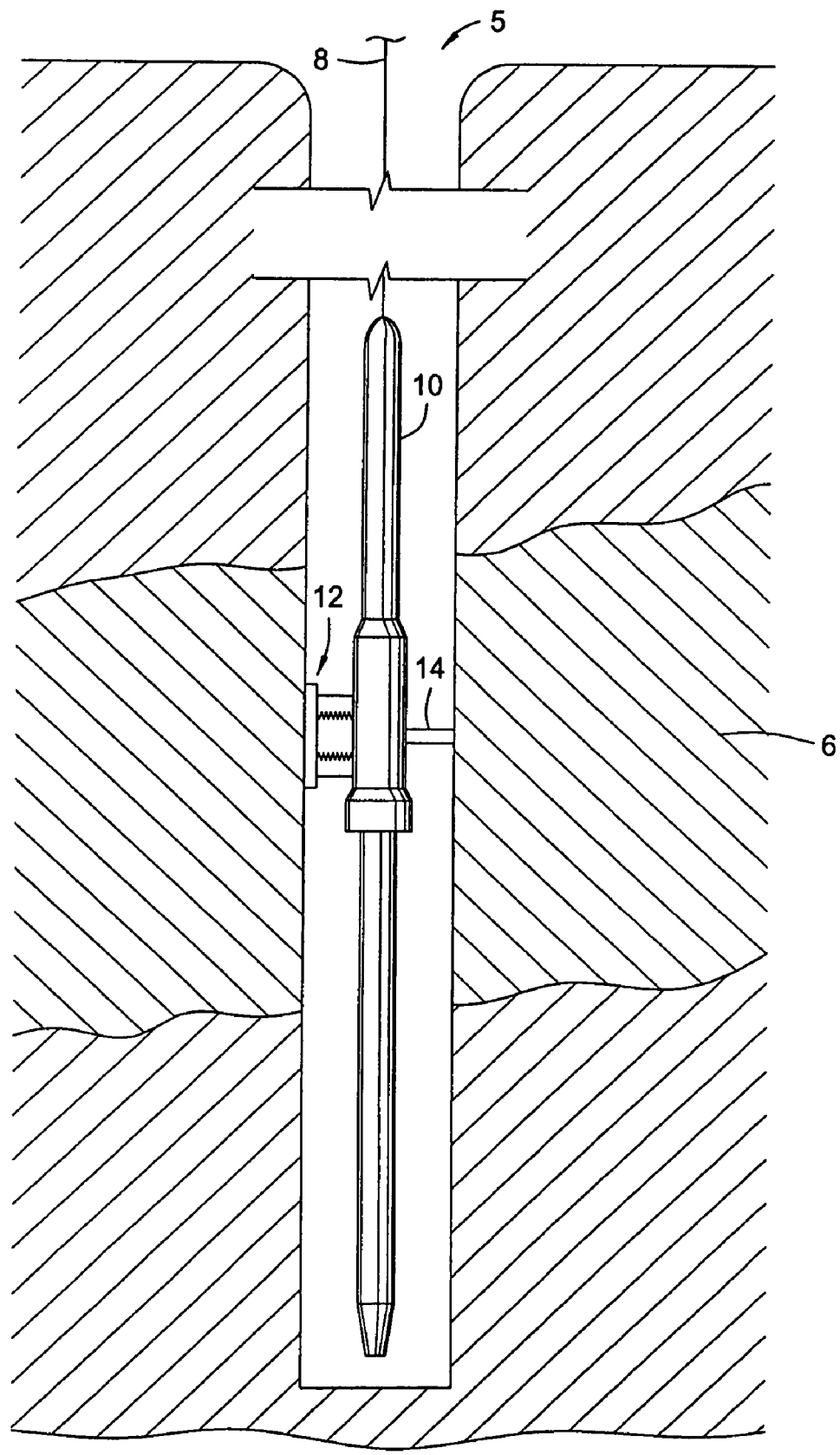
FIG. 1 portrays a sampling sonde disposed in a cut-away of a wellbore.

In one alternative of the present device, the sampling system 22 is combined with the sonde 10 and in fluid communication with the sample port 14. In this embodiment, connate fluid from the formation 6 is collected by the sample port 14 and delivered to the container 20 for analysis of the fluid. When used in conjunction with the sonde 10, the sampling system 22 is preferably housed within the sonde 10 during deployment and operation of the sampling system 22. Combining the sampling system 22 with the sonde 10 provides the advantage of "real time" sampling and reduces the risk of allowing changes in either the pressure or the temperature of the fluid that could in turn affect the sampling results. However, use of the sampling system 22 is not limited to the fluid collection apparatus of FIG. 1, but can be used with any type of device or circuit used in collecting downhole connate fluid.

In one non-limiting example of operation of the present method disclosed herein, connate fluid is drawn into the sample port 14 of a downhole sonde 10. The fluid is then introduced into the container 20 for subsequent analysis. The signal generator 16 is then activated so that a signal 17, such as one or more acoustic pulses, is generated. For the purposes of convenience the generated signal 17 is illustrated as a series of curved lines emanating from the transducer 16. After leaving the signal generator 16, the signal 17 passes through the first and second walls (24, 26) of the container 20, into the contained fluid 18, and onto the distal third and fourth walls (28, 30). A portion of the generated signal 17 (the reflected signal 19) reflects back to the direction of the signal generator 16. Similarly, the reflected signal 19 is illustrated for convenience as a series of curved lines directed towards the signal generator 16. In the embodiment of FIG. 2, the signal generator 16 can operate as a transmitter and also as a signal receiver. Optionally a separate transducer (not shown) could be included that operates solely as a signal receiver for receiving the reflected signals 19.

When the signal generator is a piezoelectric transducer, a short voltage spike can be applied to the transducer that typically lasts about 1-2 microseconds. This spike causes the transducer to resonate at its resonant frequency, which is typically from about 5 MHz to about 10 MHz. Analogous to a bell that rings for a while after it has been struck by a hammer, the transducer rings, primarily at its resonant frequency, for about a microsecond. An ever-decreasing portion of this microsecond-long pulse bounces back and forth between the tube wall that is bounded by surface 24 and surface 26, (which is in contact with the transducer 16) because a portion of the pulse is transmitted into the fluid upon each bounce off surface 26. The transmitted portion of the pulse passes beyond surface 26, enters the fluid 18, reflects from the surface 28, and eventually returns to be detected by the transducer 16. The acoustic transducer serves both as source and receiver. A high-speed (40-70 MHz) analog-to-digital converter monitors the signal received by the transducer.

As shown, the signal generator 16 receives and records the reflected signal for subsequent analysis. The recorded signal can either be immediately processed to determine fluid data, transmitted from the sonde 10 to a separate site for storage or data processing, or can be recorded within the sonde 10 for later analysis. As is known, the sound speed (c) of the liquid is determined by dividing the travel time of the signal through the fluid 18 by the distance the signal traveled through the fluid. This can be accomplished by designating the letter "d" as the distance between surface 26 and 28. Moreover, the variable 2t can be designated as the time difference between the arrival time of the first echo (corresponding to one round trip going from surface 24 to 26 and back again to 24) and the arrival time of the echo off surface 28 (corresponding to one round trip from 24, past 26, to 28, and eventually, back to 24). Therefore, 2t is amount of time it took sound to travel a round-trip distance, 2d, within the fluid from surface 26 to surface 28 and back to surface 26. The sound speed therefore is d/t.

Fluid density, can be determined acoustically from the following relationship for an acoustic pulse bouncing back and forth between surface 24 and surface 26:

$$\rho_F = \rho_W(c_W/c_F)[1+\text{Sqrt}(R_{WF})]/[(1-\text{Sqrt}(R_{WF})];\qquad(1)$$

where:
$\rho_W$=Transducer wall density in g/cc,
$\rho_T$=Transducer density in g/cc
$c_W$=Tube wall longitudinal sound speed,
$c_T$=Transducer longitudinal sound speed
$\rho_F$=Fluid density in g/cc,
$c_F$=Fluid sound speed,
$R_{WF}$=Fraction of energy reflected at all/Fluid interface, and
$R_{WF}=(\rho_W c_W - \rho_F c_F)^2/(\rho_W c_W + \rho_F c_F)^2$.

The details of acoustically determining fluid density can be found in pending patent application Ser. No. 10/801,473 filed on Mar. 16, 2004, the entirety of which is incorporated for reference herein. Fluid density could also be measured by using flexural mechanical resonators as described in U.S. patent application Ser. No. 10/144,965 filed on May 14, 2002 entitled "Method and Apparatus for Downhole Fluid Characterization Using Flexural Mechanical Resonators" by Rocco DiFoggio which is incorporated herein by reference and claims priority from U.S. Patent application Ser. No. 60/291,136 filed on May 15, 2001 entitled "Method and Apparatus for Downhole Fluid Characterization Using Flexural Mechanical Resonators" by Rocco DiFoggio. Fluid density could also be determined by any other means such as by measuring the pore pressure gradient across the zone from which the fluid is being extracted. Knowing the fluid's density and measuring its sound speed allows determination of the fluid's compressibility, which is much simpler than the current method of determining compressibility downhole by trapping a volume of fluid, expanding the volume, and measuring the drop in pressure per volume increase.

The bulk modulus B of a fluid is equal to the reciprocal of the compressibility of the fluid, B=1/K. It is also known that the sound speed is equal to the square root of the fluid's bulk modulus divided by the fluid density, $c=(B/\rho)^{1/2}$. Substituting the reciprocal of compressibility for the bulk modulus and isolating compressibility yields the following equation:

$$K=1/(c^2\rho)\qquad(2)$$

Accordingly, having determined the fluid density, $\rho$, and the fluid sound speed, c, as described herein, the fluid compressibility can then be calculated using equation (2).

In one embodiment of the method and apparatus herein disclosed, the raw amplitude data can be first processed by applying a digital bandpass filter to reject any frequencies that are not close to the acoustic source frequency. For example, for a 10 MHz acoustic source and a 40 MHz sampling frequency, one could apply a 9-11 MHz digital bandpass filter. Next, one can compute the square of the amplitude at each sampling time, which corresponds to the energy received at that time. Then, one can generate a cumulative sum of squares (CSS) of these amplitudes, which is the cumulative sum of energy received up until that time. The digital bandpass filtering and cumulative sum of squares have already smoothed the raw data and removed some noise. We can further smooth the filtered cumulative sum of squares data and also take the first and second derivatives of the CSS using the Savitzky-Golay method (Savitzky and Golay, Analytical Chemistry, Vol. 36, No. 8, July 1964). The resulting data can be further processed by using a variable threshold method. Smoothing the data and the utilization of the Savitzky-Golay method help to reduce noise from the desired signal. The variable thresholding method serves to distinguish recorded signals emanating from the far wall of the vessel or container 20 from signals received that emanate from within the near wall (between surfaces 24 and 26) of the vessel or container 20.

Figure 3:
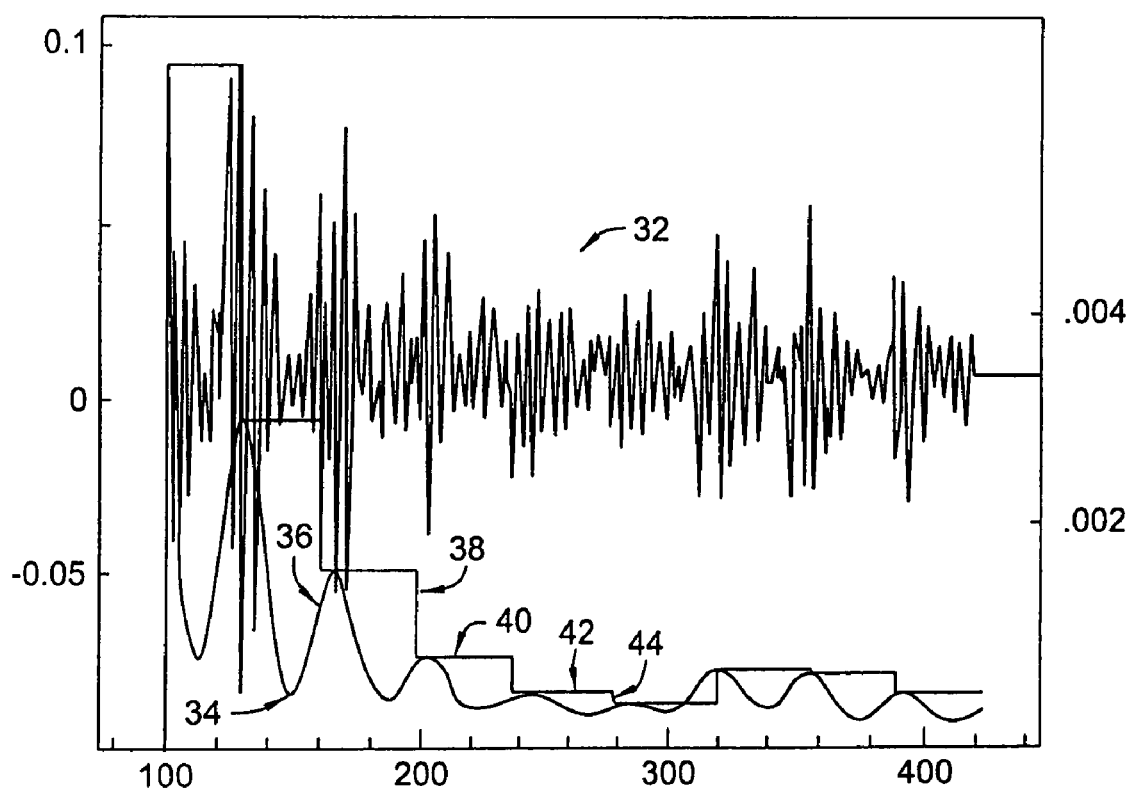
FIG. 3 represents plots containing raw data and processed data.

With reference now to FIG. 3, there is illustrated a plot having a raw data plot 32, a smooth data plot 34, and a variable threshold plot 38. In FIG. 3, the portion of the raw data has been redacted (as well as the corresponding smoothed and threshold data) that corresponds to the ringing of the transducer immediately after it receives a high voltage spike. This plot shows sampling of the signal amplitude at discrete intervals (digital data). To avoid aliasing, the sampling rate is several times the acoustic source frequency. After recording the data, the square of the amplitude for each channel is computed. The amplitude for each channel is proportional to the acoustic intensity (energy) that was received at that channel's time. Next, the cumulative sum (the "integral") of these squared amplitudes is calculated.

The data smoothing is further accomplished by computing the first derivative with respect to time of the cumulative sum of squares using Savitzky-Golay (SG) coefficients, which helps create smoothed numerical derivatives. Enhanced smoothing is accomplished by using Savitzky-Golay coefficients of lower order (such as square or cube) polynomials over a fairly large number of points (25 channels). The first derivative of the cumulative sum of squares is the smoothed energy received versus time, which shows distinct acoustic energy pulses. The resulting values produced by the Savitzky-Golay method are shown plotted in the smooth data plot 34 of FIG. 3.

In order to determine the local maxima and minima of the first derivative, the second derivative is taken of the cumulative sum of squares using Savitzky-Golay (SG) coefficients of a low order and a large number of points. The local maxima (pulse energy peaks) of the first derivative curve can be used to indicate the time at which a particular pulse reflection is received by the receiving transducer 16. It should be pointed out that the second derivative crosses zero when the first derivative reaches either its local maxima or minima. A pulse peak occurs between two channels whenever the second derivative changes from positive (in the left channel) to negative (in the right channel) with increasing time and the first derivative exceeds some variable threshold, which is described in detail later. Subchannel time resolution can be achieved by interpolating so as to estimate the location between two channels where the second derivative crosses zero. Alternatively, energy maxima can be distinguished from energy minima (both of which correspond to zeros of the second derivative of the CSS) based on the sign of the third derivative of the CSS.

Using the data obtained from the processed signal, the sound speed of the wall of the vessel or container 20 is twice the wall thickness divided by the (round-trip) time between reverberation pulse peaks within the tube wall. The wall sound speed may change with temperature or with pressure of the fluid inside the tube thus causing the wall's acoustic impedance to change. The wall's acoustic impedance must be known to compute fluid density from fluid sound speed and the decay rate of within-wall pulse echo reverberations. Direct downhole measurement of the wall's sound speed can be made from the wall thickness and the time between within-wall pulse peak reverberations. The wall speed is one parameter used to calculate the density of whatever fluid is in contact with the wall. Another factor in calculating fluid density is the wall density but changes in the wall's density with temperature and pressure are a much smaller effect that can usually be ignored or estimated from a table.

The smooth data plot 34 comprises reflected signals both from signal reverberations within the near wall (between the first and second wall 24 and 26) as well as a reflection from the far wall (third wall 28). These reflected signals are illustrated as curves 36 on the smooth data plot 34. The acoustic signal reverberating within the near wall decays over time, this can be seen in the decreasing local maxima of the curves 36 of the smooth data plot 34 of FIG. 3. However, the amplitude of the signal reflected from the far wall (third wall 28) will exceed the amplitude of the last observable within-wall reverberation. Based on this, the variable threshold method can be used to determine the time (channel number) at which the far wall reflection pulse reaches its peak energy. Conceptually, the threshold keeps being lowered to the height of the last within-wall reverberation peak. The first pulse peak whose amplitude increases from its predecessor is taken as the far wall reflection.

In an embodiment of the present method, the variable pulse-peak-detection threshold function is generated using two passes. On the first pass, the threshold value for each channel is the largest energy (first derivative of CSS) value that occurred in the previous M channels, where M is the number of channels between peaks of energy pulses reverberating within the wall. This first pass for creating a variable threshold generates a staircase-like function (not shown) having horizontal steps joined by rises and falls that are not perfectly vertical. A graphical representation of the second pass is shown comprising a series of steps 40 having horizontal steps 42 and vertical sections 44. The vertical sections 44 are adjusted to be substantially vertical (i.e. have an infinite slope) while keeping the horizontal steps 42 substantially the same except for extending them left or right. This is accomplished by extending each horizontal step 42 leftward to the last channel of a higher step whenever a higher step 42 lies to its left.

Similarly, when a higher step 48 lies to the right of an adjacent lower step 46, the lower step 46 is extended rightward to the first channel of the higher step 48. Completion of the second pass generates a variable threshold that looks like a staircase whose vertical sections have a substantially infinite slope. Since the peaks of the inner-wall reverberation pulses get smaller over time, the first pulse whose peak increases over its predecessor's peak must be the signal that is reflected from the far wall (third wall 28). Accordingly, fluid sound speed is twice the fluid-filled gap distance divided by the round trip time between the first within-wall reverberation and the far-wall reflection. One of the many advantages of the ability to distinguish between signals representing near wall reverberations and signals that represent far wall reflections is that the signal generator 16 can be positioned within the confines of the vessel or container 20, on its outer circumference, or even within the body of the container 20 (i.e. between the first and second walls 24 and 26 or between the third and fourth walls 28 and 30).

An additional advantage to using the device and method disclosed herein is the ability to determine if the analyzed fluid contains gas or is at its bubble point. Gases always attenuate sound much more than liquids. The presence of any separate gaseous phase highly attenuates acoustic signals. Thus, if the reflected signal 19 is non-existent or very weak, this condition can indicate that the sampled fluid 18 contains some separated gaseous phase (bubbles) or consists primarily of a gaseous phase. It should be pointed out that with regard to acoustic signals, attenuation increases as the square of the frequency according to the classical acoustic attenuation equation derived by Stokes and Kirchhoff. Gas dissolved in a liquid will not have the same high attenuation of acoustic energy as do free gas bubbles or 100% gas. However, the more gas that is dissolved in a liquid, the higher the compressibility. Therefore, for petroleum fluids, sound speed could be used to estimate a crude oil's gas oil ratio (GOR), which is always expressed in Standard Cubic Feet of Gas per Stock Tank Barrel of Crude Oil. For example, Terra Bulloch (1999 Masters Thesis, Michigan Technological University) calculated that, at 6000 psi and 85 C, the sound speed of a particular live crude oil drops quite linearly from approximately 1370 m/sec (for GOR=80) to approximately 915 m/sec (for GOR=1300). Accordingly, to determine the presence of gas bubbles within a fluid sample, acoustic signals generated into the fluid should exceed 100 kHz so as to be attenuated below the detection level of the instrument within the pathlength of a few millimeters of fluid between 26 and 28. To keep the acoustic wavelength small compared to the short distance between 24 and 26, the acoustic frequency should be substantially in the range of about 5 MHz to about 10 MHz.

Determination of the bubble point of the sampled fluid could involve operating the sampling system 22 as described above while at the same time reducing the pressure of the fluid 18. Assuming reflected signals 19 are measured at the start of the bubble point test, the corresponding bubble point pressure could be determined at the time when reflected signals 19 are no longer measurable despite generating signals 17. For electrically-insulating fluids, sound speed could also be used to estimate the fluid's thermal conductivity using Bridgman's equation, which states that the thermal conductivity is proportional to the speed of sound times Boltzman's constant (1.38E10-23 Joule/degree Kelvin) times the number of molecules per unit volume. The proportionality constant can range from about 2.8 to about 3.0. Knowledge of a fluid's thermal conductivity can be useful for estimating subsurface temperature gradients in a geothermal reservoir, evaluating heat losses during thermally induced enhanced oil recovery process, and determining heat losses from underground fluid. Sitakanta Mohanty, *J. Phys. D Appl. Phys.* 30 No 24 (21 Dec. 1997).

It should be pointed out that other data processing methods could be used in conjunction with the methods described herein. For example, an additional step of alternatively determining sound speed by the traditional cross correlation technique could be done once the approximate time of arrival of the far wall reflection has been determined by the variable threshold technique.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, production of the generated signal 17 is not limited to a signal generator 16 disposed within or adjacent to the sampling system 22, but could include signal generators from remote sources. The remote signal sources could be from ballistics, geophones, airguns, or any other known signal-generating source. These and other similar modifications will readily suggest themselves to those skilled in the art, and are intended to be encompassed within the spirit of the present invention disclosed herein and the scope of the appended claims.

What is claimed is:

1. A method of estimating a fluid property comprising:
   generating an acoustic signal that propagates a distance through a fluid and reflects off at least two surfaces that are a known distance apart to create at least two reflected acoustic signals, the two surfaces being substantially parallel;
   recording the reflected acoustic signals;
   calculating the cumulative sum of squared (CSS) amplitudes of the reflected acoustic signals;
   calculating second derivatives of the CSS amplitudes using Savitzky-Golay coefficients; identifying pulse peaks from the points in time when the second derivatives of the CSS changes sign, wherein the pulse peaks represent the points in time when the reflected acoustic signals were recorded; and
   determining the fluid sound speed based on the time differences between the pulse peaks and the known distance differences.

2. The method of estimating a fluid property of claim 1 further comprising determining fluid density based on the fluid sound speed.

3. The method of estimating a fluid property of claim 1 further comprising positioning fluid between the surfaces proximate to a signal generator and activating the signal generator thereby creating acoustic signal reverberations through the fluid.

4. The method of estimating a fluid property of claim 1 wherein the step of generating a signal is performed with a device comprising a piezoelectric device.

5. The method of estimating a fluid property of claim 1 further comprising determining the gas oil ratio based on the fluid sound speed.

6. The method of estimating a fluid property of claim 2, further comprising estimating a value of fluid compressibility, wherein the value of the fluid compressibility is the reciprocal of the product of the fluid sound speed squared and the fluid density.

7. The method of estimating a fluid property of claim 1 further comprising determining the presence of gas within the fluid.

8. The method of estimating a fluid property of claim 7, wherein the presence of gas is detected based on a signal strength ranging from no response to a low response.

9. The method of estimating a fluid property of claim 1 further comprising processing the measured signal with a variable threshold method.

10. The method of claim 1 wherein the recorded reflected signal is measured at discrete data points to form raw data, the method further comprising squaring the value of each discrete data point.

11. The method of claim 1, wherein the Savitzky-Golay coefficients extend up to the third order.

* * * * *